United States Patent [19]

Banasiak

[11] Patent Number: 4,560,792

[45] Date of Patent: * Dec. 24, 1985

[54] DISPROPORTIONATION OF FUNCTIONAL OLEFINS

[75] Inventor: Dennis S. Banasiak, Bartlesville, Okla.

[73] Assignee: Phillips Petroleum Company, Bartlesville, Okla.

[*] Notice: The portion of the term of this patent subsequent to May 26, 1998 has been disclaimed.

[21] Appl. No.: 400,188

[22] Filed: Jul. 20, 1982

[51] Int. Cl.$^4$ .................. C07C 67/08; C07C 67/333; C07C 41/32; C11C 3/02

[52] U.S. Cl. .................. 560/261; 260/410.9 N; 568/449; 568/687; 568/877

[58] Field of Search .................. 568/687, 449, 877; 560/261; 260/410.9 N

[56] References Cited

U.S. PATENT DOCUMENTS

| | | | |
|---|---|---|---|
| 3,794,196 | 8/1976 | Nakamura et al. | 560/261 |
| 3,917,711 | 11/1975 | Roelofs et al. | 424/84 |
| 4,083,995 | 4/1978 | Mitchell et al. | 424/311 |
| 4,233,230 | 11/1980 | Otton | 260/410.9 N |
| 4,269,780 | 5/1981 | Banasiak | 560/261 |

FOREIGN PATENT DOCUMENTS 2085881  4/1982  United Kingdom ................ 560/261

OTHER PUBLICATIONS

Levisalles et al., "Tetrahedron", vol. 36 (1980), pp. 3181-3185.
Nakamura et al., "Chemistry Letters", (1976), pp. 1019-1024.
Nakamura et al., "Chemistry Letters," (1977), pp. 1227-1230.
Baker et al., "Tetrahedron Letters", (1977), pp. 441-442.
Nakamura et al., "Chemistry Letters," (1976), pp. 253-256.

*Primary Examiner*—J. E. Evans
*Attorney, Agent, or Firm*—Edward L. Bowman

[57] ABSTRACT

A process for producing functional monoolefins having specific types of cis to trans ratios involving disproportionating a functional monoolefin with a hydrocarbyl monoolefin consisting essentially of either (1) an internal olefin or (2) a terminal olefin. Also disclosed are functional olefin compositions useful in controlling insects.

19 Claims, No Drawings

DISPROPORTIONATION OF FUNCTIONAL OLEFINS

BACKGROUND OF THE INVENTION

This invention relates to the disproportionation of functional olefins and to the products resulting therefrom.

The disproportionation of olefins containing other functional groups is a very desirable technique for obtaining valuable chemicals that otherwise would require multistep preparations that are costly and often give products that are difficult to purify. The disproportionation of olefins containing ester and ether groups is particularly interesting in that it provides a route to chemicals having potential application in insect control because of the ability of the compounds to disrupt the mating of specific insects.

It has been noted by those working in the area of insect pheromones that the microstructure ratio of functional olefins can often have a significant influence upon the effectiveness of a particular functional olefin as an insect control agent. Thus, while some insects are attracted to a trans isomer, others may be attracted to a cis isomer, and still others may be best attracted by a particular molar ratio of cis and trans isomers.

A particularly useful catalyst system for the production of functional olefins has been disclosed in U.S. Pat. No. 4,269,780, the disclosure of which is incorporated herein by reference. The present invention is based upon the discovery that by selecting the proper reactants, it is possible to vary the isomer ratio in the recoverable functional olefin disproportionation product.

SUMMARY OF THE INVENTION

In accordance with the present invention, a monoolefin having at least one terminal ester or ether group is reacted with a hydrocarbyl monoolefin consisting essentially of either an internal olefin or an alpha-olefin having at least three carbon atoms in the presence of a catalyst comprising a neutral tungsten carbene and a metal halide promoter.

DETAILED DESCRIPTION OF INVENTION

The present invention deals with the cross-disproportionation of a monoolefin having at least one terminal functional group selected from groups having the formulas

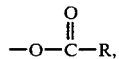

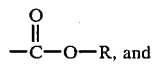

wherein R is a hydrocarbyl group having 1 to 20 carbon atoms or in the case of the first formula hydrogen. Thus, the functional olefins include alkenyl acid esters, alkenyl esters, and alkenyl ethers. The preferred functional monoolefins are those wherein the olefinic hydrocarbyl portion thereof has the formula

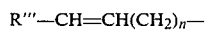

wherein n is in the range of 2 to 20, R''' is hydrogen or an alkyl radical having 1 to 20 carbon atoms. It is also within the scope of the present invention to use a functional monoolefin having two terminal functional groups of the types described above. Typically, the preferred functional monoolefins contain no more than about 30 carbon atoms per molecule.

The other olefin reactant in the inventive disproportionation consists essentially of either (1) an internal hydrocarbyl monoolefin or (2) a hydrocarbyl alpha-monoolefin having at least three carbon atoms per molecule. When an internal monoolefin reactant is employed, it has been noted that as a general rule the level of trans isomer in the product is higher than that produced using an alpha-monoolefin capable of producing a compound having the same chemical formula. The currently preferred hydrocarbyl monoolefins are those having no more than about 20 carbon atoms per molecule.

If a symmetrical difunctional monoolefin reactant is used that is substantially all in the trans form, the product obtained consists predominately of the trans isomer regardless of whether an internal or alpha-olefin is used in the cross-disproportionation. By using such a technique, it has been found that it is possible to produce unsaturated functional olefins that are substantially all trans. This is particularly surprising since disproportionation reactions are generally expected to provide a mixture of cis and trans isomers.

The catalyst system employed in the present invention comprises a neutral carbene complex and a metal component which acts as a promoter for the neutral carbene complex.

Typical neutral carbene complexes for use in the catalyst system are those having the formula

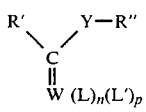

wherein R' is selected from the group consisting of alkyl or cycloalkyl radicals containing 1 to 10 carbon atoms per radical and aryl or substituted aryl radicals containing 6 to 30 carbon atoms per radical wherein the substituted radicals can have one or more substituents, each of which can be the same or different and selected from the group consisting of halides, alkoxides, and alkyl radicals containing 1 to 20 carbon atoms; Y is S or O; R'' is selected from the group consisting of alkyl, cycloalkyl, aryl, and substituted aryl radicals containing 1 to 30 carbon atoms per molecule and wherein the aryl substituents are as described for R' and wherein if Y is S only one of R' and R'' is aryl or substituted aryl; each L is a neutral ligand individually selected from CO, NO, PR'$_3$, PCl$_3$, PF$_3$, and pyridine, where R' is as defined above, and L' is cyclopentadienyl; p is 0 or 1; and n is 5 when p is 0 or 2 when p is 1.

The metal component employed as a promoter for the carbene is selected from the group consisting of the chlorides and bromides of the metals of Groups IVa, IVb, Vb, VIb, VIIB, VIII, and Ib and the oxychlorides and oxybromides of molybdenum, tungsten, vanadium, and chromium; wherein if the metal is vanadium it is in an oxidation state of either 4 or its highest, stable, common, ionic oxidation state; if the metal is molybdenum, tungsten, or rhenium it is in an oxidation state of either 5 or its highest, stable, common, ionic oxidation state; and if the metal is not vanadium, molybdenum, tungsten or rhenium the metal is in its highest, stable, common, ionic, oxidation state. The molar ratio of the metal component can vary over a wide range with varying effects upon yield and selectivity. Typically, the molar ratio of the metal component to the carbene complex is in the range of about 1/1 to about 500/1, preferably in the range of about 2/1 to 25/1. In a particularly preferred embodiment, the promoter comprises a combination of a tin tetrahalide and a tetrahalide of either silica or germanium. The molar ratio of silica or germanium tetrahalide to tin tetrahalide is generally in the range of about 0.5/1 to about 20/1, most preferably generally about 2/1.

The amount of catalyst employed in the process of this invention can be expressed in terms of the molar ratio of olefin to carbene complex component. Generally, the molar ratio of the total stoichiometric amount of olefinic reactant to carbene complex component is in the range of about 1/1 to about 5000/1 and preferably from about 50/1 to about 2000/1. This term "total stoichiometric amount" is used herein to denote the moles of reactant that could theoretically react so as to distinguish from cases when two or more olefins are employed and one or more is used in a greater amount than will react. Thus, the amount of catalyst is generally based upon the amount of reactive olefins and not on excess olefin.

The disproportionation reaction of this invention can be carried out at temperatures between 35° C. and about 200° C. While lower temperatures can be used, the reaction rates are generally too low to be of interest. Temperatures above 200° C. can be used, but excess decomposition of the reaction components can occur. The preferred reaction temperatures are from about 50° C. to about 125° C.

The pressure during the disproportionation reaction can be from about atmospheric to about 5000 psig (34470 KiloPascals, kPa). Preferably, the pressure is from about atmospheric to about 1000 psig (6894 kPa).

The disproportionation reaction can be carried out in the presence of diluents such as saturated hydrocarbons, e.g., hexane, octane, cyclohexane, aromatic hydrocarbons, e.g., benzene, toluene, or halogenated compounds, e.g., chlorobenzene, chloroform, methylene chloride, bromoform, and the like.

The amount of diluent can be expressed as a volume ratio of diluent to the olefin. Suitable volume ratios of diluent to olefin can be from about 0/1 to about 500/1 and preferably from about 1/1 to about 300/1.

The presence of oxygen and water has been found to be deleterious to the disproportionation reaction and should be substantially avoided during the reaction. Inert gases such as nitrogen, argon or helium can be used to maintain a dry, inert atmosphere during the reaction.

The metal compounds used as components of the catalyst system should be pure, free of oxygen or water, and free of any hydrolysis products. In general, the yield of disproportionation product decreases as the metal compound purity decreases.

The functional olefins used in the disproportionation reaction should be dry and free of polar materials such as carboxylic acids or alcohols. A purification step to remove impurities by such methods as filtering through silica gel or alumina and storing over molecular sieves or distilling from suitable drying agents is beneficial.

The reaction time period depends on the reaction temperature and pressure as well as on the nature of the particular catalyst system and olefinic reactant used. The reaction time is generally from about 30 minutes to about 120 hours.

A still better understanding of the present invention and its advantages will be provided by the following examples.

The non-functional and functional olefins used in the following examples were commercial materials which were usually distilled, contacted with silica gel or alumina and stored over 4 A molecular sieves. Diluents were usually distilled from the appropriate drying agent and stored over 4 A molecular sieves. The various metal halides and organometallics were commercial materials which were normally used without further purification, but with careful exclusion of moisture and oxygen. In several cases, fresh reagents were found to give better disproportionation results than older reagents which are believed to have changed in chemical composition, for example by hydrolysis during aging. During the reaction evaluations, it was found that the careful exclusion of oxygen and moisture from the reaction system was extremely important for successful disproportionation results.

The carbene complexes were prepared by published procedures. Typically, they were prepared by reacting the appropriate metal carbonyl with an organolithium compound and then adding a trialkyloxonium tetrafluoroborate. For example, tungsten hexacarbonyl was reacted with phenyllithium and was then reacted with trimethyloxonium tetrafluoroborate to form (methoxyphenylcarbene)pentacarbonyltungsten(O)

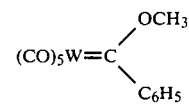

The carbene complexes were stored in a desiccator in a freezer before use in a reaction.

Some of the runs in the following examples were carried out in 10 oz. or 32 oz. beverage bottles equipped with a magnetic stirrer, a self-sealing elastomeric cap liner, and a three-hole crown cap. The liquid reaction components were charged to the dried, nitrogen flushed bottle by syringe through the cap. Solids were added to the bottle before attaching the cap. The reaction mixture was heated to the desired temperature and stirred at the reaction temperature for the desired time period. Venting was accomplished by means of a syringe needle through the bottle septum. The needle is attached to an oil filled bubble-tube capped with a Drierite filled drying tube.

Some of the runs in the following examples were carried out in 300 mL or 1000 mL Hastelloy C magnadrive packless autoclave. A side port on each autoclave was equipped with a ball valve to allow passage of a syringe needle into the autoclave. In some runs the reactions were vented by manually opening a valve to allow the autoclave to vent to the desired lower pressure. In other runs, venting was accomplished by means of a variable pressure relief valve which was self-sealing if the pressure dropped below the set pressures.

The autoclave was sealed empty, purged with dry nitrogen and heated to 150° C. or higher for at least one hour, then cooled under a nitrogen sweep to room temperature. The autoclave was left sealed under at least 30 psig $N_2$ and left overnight (for convenience the reactor was dried the day before use). The next day a slight N$_2$ sweep was again started and the reagents added by syringe through a ball valve which was also the nitrogen vent. The order of reagent addition does not appear critical but the following order was utilized: (1) solvent; (2) olefins; (3) solution of carbene; and (4) solutions of cocatalysts. GC standards were added prior to the olefins or if the standard could not be tolerated by the catalyst, at the end of reaction. The ball valve was then closed and the reactor pressurized with nitrogen to the desired pressure. Heating by means of an external heater and stirring were then started. (Temperatures were controlled by means of either a Thermoelectric #400 or an Eurotherm Temperature Controller. Temperatures were determined with Type J thermocouples placed in the autoclave thermowell and were read from an Acromag Temperature Indicator. Pressure readings were made visually from gauges on the autoclave.) Heating and stirring were continued for 2 to 8 hours. Time of reaction was measured from the point reaction temperature was reached, thus, the overall time the reagents were heated in the reactor was somewhat longer than indicated. When the desired time of reaction was reached the heater was removed and compressed air was used to cool the exterior of the reactor. The reactor was then vented to atmosphere and opened. The reaction mixture was removed. Analysis and work up was the same as that of the beverage bottle reactions.

Reactions carried out at atmospheric pressure were run in an oven-dried 3-neck flask (1, 3, 5, and 12 liter flasks were employed). The flask was equipped with a magnetic or a mechanical stirrer, a dry ice or water condenser and a septum inlet. Once sealed, the reactor was flushed with a nitrogen flow and kept under a nitrogen atmosphere while the reagents (carbene plus metal halide catalyst components, solvent, functional olefin reactant) were added. The flask was then heated to the desired reaction temperature, typically about 80° C., and introduction of the gaseous olefinic reactant was begun via the septum inlet.

Alternatively, the carbene plus metal halide catalyst components and solvent could be charged to the reactor first, then the olefinic reactant introduced and allowed to react for a period of time before the functional olefin reactant is introduced. In this manner, an alpha-olefin reactant, such as 1-butene, can be converted, in situ, to an internal olefin (3-hexene) which typically gives a higher trans-content product when cross-disproportionation of a functional and non-functional olefin is carried out.

Yields were determined by gas chromatography (G.C.) employing internal standard. Yields are calculated based on the amount of functional olefin charged as that is generally the limiting reagent. A Perkin Elmer Sigma 3 chromatograph with flame ionization detector was used. Either a ⅛ in×10 ft 10% OV225 on Chromosorb P or a ⅛ in×10 ft 10% Altech CS-8 on Chromosorb W-AW column was employed. Cis-trans determinations were accomplished using a ¼ in×16 ft 15% Silar 10C glass column, and were confirmed by C-13 analysis of isolated product.

For product isolation, the reactor contents were diluted with solvent, then treated with enough 10% aqueous ammonium hydroxide to precipitate the transition metal complexes. The solution, normally yellow in color, was filtered. The organic layer was washed with water, and then with water saturated with sodium chloride, and dried over anhydrous magnesium sulfate. The dried organic layer was then filtered and solvent removed. The residue thus obtained was ready for distillation.

EXAMPLE I

9-Tetradecenyl Acetate from 1-Hexene and 9-Decenyl Acetate

A series of runs were carried out for the preparation of 9-tetradecenyl acetate from 1-hexene and 9-decenyl acetate. Except as noted in Table I, the carbene employed was (methoxyphenylcarbene)pentacarbonyltungsten(O), and the metal halide catalyst component consisted of a mixture of SnCl$_4$ and SiCl$_4$. Reagent quantities employed, reaction conditions and reaction results are presented in Table I.

TABLE I

| Run # | 1-Hexene, Mol | Acetate, Mol | Catalyst, Mol | | Diluent, ml | | Time Hrs. | Temp., °C. | Press., psig | Yield | trans/cis |
|---|---|---|---|---|---|---|---|---|---|---|---|
| | | | Carbene | SnCl$_4$/SiCl$_4$ | | | | | | | |
| 1 | 0.22 | 0.22 | 0.001 | 0.022/0.044 | C$_6$H$_5$Cl | 70 | 4 | 80 | 80 | 8.6 | 1.8 |
| 2 | 0.22 | 0.11 | 0.001 | 0.022/0.044 | C$_6$H$_5$Cl | 90 | 4 | 82 | 80 | 14.4 | 2.0 |
| 3 | 0.44 | 0.22 | 0.004 | 0.088/0.166 | C$_6$H$_5$Cl | 180 | 4.5 | 82 | 5 | 28.3 | 3.2 |
| 4 | 0.44 | 0.22 | 0.001 | 0.022/0.044 | C$_6$H$_5$Cl | 90 | 4.5 | 84 | 10 | 38.6 | 3.1 |
| 5 | 0.44 | 0.11 | 0.001 | 0.022/0.044 | C$_6$H$_5$Cl | 90 | 4.5 | 85 | 3 | 28.4 | 3.0 |
| 6 | 0.44 | 0.22 | 0.001 | 0.022/0.044 | C$_6$H$_5$Cl | 90 | 4.5 | 82 | 10 | 39.6 | 2.8 |
| 7 | 0.44 | 0.11 | 0.001 | (WCl$_6$) 0.002 | Hexane | 115 | 4 | 104 | 60 | 11.7 | 1.5 |
| 8 | 0.44 | 0.22 | 0.001 | 0.01/0.02 | C$_6$H$_5$Cl | 100 | 4 | 80 | 20 | 6.3 | 1.6 |
| 9* | 0.88 | 0.44 | 0.002* | 0.02/0.04 | C$_6$H$_5$Cl | 200 | 5 | 79 | 5 | 3.5 | 1.9 |
| 10** | 0.44 | 0.22 | 0.002** | 0.02/0.04 | C$_6$H$_5$Cl | 100 | 5 | 78 | 5 | 0.7 | n.d. |
| 11 | 1.78 | 0.89 | 0.0033 | 0.033/0.099 | Hexane | 200 | 5 | 79 | 10 | 24.6 | 1.8 |
| 12 | 1.88 | 0.89 | 0.002 | 0.04/0.08 | C$_6$H$_5$Cl | 160 | 4.5 | 77 | 5 | 10.5 | 1.3 |
| 13 | 1.78 | 0.89 | 0.0022 | 0.022/0.044 | C$_6$H$_5$Cl | 210 | 5 | 81 | 5 | 18.8 | 1.5 |
| 14 | 0.44 | 0.22 | 0.001 | 0.01/0.02 | C$_6$H$_5$Cl | 47 | 7 | 85 | 10 | 29.5 | 1.7 |
| 15 | 0.44 | 0.22 | 0.001 | (WCl$_6$) 0.002 | C$_6$H$_5$Cl | 40 | 4 | 81 | 10 | 36.5 | 2.3 |
| 16 | 0.89 | 0.44 | 0.002 | 0.02/0.04 | C$_6$H$_5$Cl | 200 | 4.5 | 83 | 5 | 30.7 | 1.8 |
| 17 | 0.11 | 0.056 | 0.00025 | 0.0025/0.005 | Hexane | 22 | 20 | 80 | — | 25.2 | 1.8 |
| 18 | 0.89 | 0.22 | 0.001 | 0.01/0.02 | Hexane | 50 | 5 | 78 | 30 | 18.6 | 1.7 |
| 19 | 0.89 | 0.22 | 0.001 | 0.01/0.02 | C$_6$H$_5$Cl | 50 | 5 | 76 | 60 | 9.9 | 1.5 |
| 20 | 0.89 | 0.44 | 0.002 | 0.02/0.04 | Hexane | 200 | 5 | 78 | 60 | 14.4 | 1.7 |
| 21 | 1.78 | 1.78 | 0.004 | 0.04/0.08 | Hexane | 80 | 4 | 80 | 35 | 15.1 | 1.7 |
| 22 | 0.88 | 0.44 | 0.001 | 0.01/0.02 | Hexane | 150 | 5 | 81 | 30 | 15.6 | 1.7 |
| 23 | 1.78 | 0.89 | 0.004 | 0.04/0.08 | Hexane | 80 | 4 | 84 | 35 | 16.1 | 1.8 |
| 24 | 0.22 | 0.11 | 0.001 | 0.01/0.02 | C$_6$H$_5$Cl | 100 | 4 | 84 | 5 | 39.1 | 2.8 |
| 25 | 0.22 | 0.11 | 0.001 | 0.01/0.02 | C$_6$H$_5$Cl | 100 | 4 | 87 | 95 | 24.0 | 2.5 |
| 26 | 0.22 | 0.22 | 0.001 | 0.01/0.02 | C$_6$H$_5$Cl | 100 | 4.5 | 88 | 40 | 12.7 | 1.7 |
| 27 | 0.44 | 0.11 | 0.001 | 0.01/0.02 | C$_6$H$_5$Cl | 100 | 4 | 87 | 20 | 36.0 | 2.8 |

TABLE I-continued

| Run # | 1-Hexene, Mol | Acetate, Mol | Catalyst, Mol | | Diluent, ml | Time Hrs. | Temp., °C. | Press., psig | Yield | trans/cis |
|---|---|---|---|---|---|---|---|---|---|---|
| | | | Carbene | $SnCl_4/SiCl_4$ | | | | | | |
| 28 | 0.22 | 0.11 | 0.0005 | 0.01/0.02 | $C_6H_5Cl$ | 90 | 4 | 81 | 10 | 21.9 | 2.0 |
| 29 | 0.88 | 0.22 | 0.002 | 0.04/0.08 | $C_6H_5Cl$ | 140 | 4 | 79 | 60 | 25.5 | 1.6 |
| 30 | 15.7 | 4.1 | 0.011 | 0.2/0.4 | $C_6H_5Cl$ | 500 | 42 | 70 | atm. | 22.8 | 1.3 |
| 31 | 0.5 | 0.05 | 0.0003 | 0.002/0.04 | $C_6H_5Cl$ | 50 | 4 | 101 | 70 | 16.3 | 1.3 |
| 32 | 0.5 | 0.12 | 0.0005 | 0.011/0.022 | $C_6H_5Cl$ | 60 | 2 | 106 | 80 | 11.0 | 1.6 |

*(ethoxyphenylcarbene)pentacarbonyltungsten(O).
**(methoxymethylcarbene)pentacarbonyltungsten(O).

The results in Table I demonstrate that the yield and trans/cis ratio of desired cross-disproportionation product is seen to vary as a function of (1) functional/nonfunctional olefin ratio (compare Runs 1, 2 and 4), (2) olefin/carbene ratio (compare Runs 12 and 14), (3) carbene/metal halide ratio (compare Runs 6 and 14), (4)

cis ratio of about 4:1 and 9-decenyl acetate. The carbene employed was (methoxyphenylcarbene)pentacarbonyltungsten(O), and the metal halide catalyst component, unless otherwise noted, consisted of a mixture of $SnCl_4$ and $SiCl_4$. Reagents quantities employed, reaction conditions and reaction results are presented in Table II.

TABLE II

| Run # | 5-Decene, Mol | Acetate, Mol | Catalyst, Mol | | Diluent, ml | Time Hrs. | Temp., °C. | Press., psig | Yield | trans/cis |
|---|---|---|---|---|---|---|---|---|---|---|
| | | | Carbene | $SnCl_4/SiCl_4$ | | | | | | |
| 1 | 0.22 | 0.22 | 0.0005 | 0.01/0.02 | $C_6H_5Cl$ | 90 | 4.5 | 84 | 40 | 20.5 | 5.0 |
| 2 | 0.22 | 0.22 | 0.001 | 0.01/0.02* | $C_6H_5Cl$ | 150 | 4 | 100 | 70 | 23.7 | 6.0 |
| 3 | 0.55 | 0.55 | 0.0025 | 0.025/0.05 | $C_6H_5Cl$ | 325 | 4.5 | 101 | 50 | 45.3 | 5.0 |
| 4 | 0.55 | 0.55 | 0.0025 | 0.025/0.05 | $C_6H_5Cl$ | 325 | 4 | 100 | 100 | 59.2 | 5.1 |
| 5 | 1.11 | 1.11 | 0.0025 | 0.025/0.05 | $C_6H_5Cl$ | 125 | 5 | 95 | 130 | 28.4 | 7.0 |
| 6 | 0.11 | 0.11 | 0.0005 | 0.01/0.02 | $C_6H_5Cl$ | 90 | 4.5 | 83 | 45 | 30.0 | 4.7 |
| 7 | 0.22 | 0.22 | 0.001 | 0.01/0.02 | $C_6H_5Cl$ | 100 | 7 | 84 | 40 | 12.9 | 5.3 |
| 8 | 0.22 | 0.22 | 0.005 | 0.01/0.01* | $C_6H_5Cl$ | 70 | 4 | 82 | 35 | 9.3 | 11.1 |
| 9 | 0.56 | 0.56 | 0.0025 | 0.025/0.04 | $C_6H_5Cl$ | 315 | 4 | 80 | 60 | 37.7 | 4.0 |
| 10 | 0.056 | 0.056 | 0.00025 | 0.0025/0.005 | Hexane | 22 | 20 | 80 | — | 45.7 | 5.0 |
| 11 | 0.42 | 0.42 | 0.002 | 0.02/0.04 | Hexane | 200 | 5 | 84 | 50 | 38.0 | 5.0 |
| 12 | 0.11 | 0.11 | 0.0005 | 0.005/0.01* | $C_6H_5Cl$ | 100 | 4 | 102 | 50 | 15.3 | 4.4 |
| 13 | 0.11 | 0.11 | 0.001 | 0.01/0.02 | Hexane | 125 | 4 | 84 | 35 | 13.7 | 7.2 |
| 14 | 0.11 | 0.11 | 0.0005 | 0.005/0.01 | $C_6H_5Cl$ | 100 | 4 | 101 | 50 | 43.6 | 4.9 |
| 15 | 0.22 | 0.22 | 0.0005 | 0.005/0.01 | Hexane | 75 | 5.5 | 98 | 80 | 12.6 | 8.0 |
| 16 | 0.11 | 0.11 | 0.001 | 0.01/0.02 | $C_6H_5Cl$ | 125 | 5 | 95 | 75 | 45.0 | 3.6 |
| 17 | 0.22 | 0.11 | 0.001 | 0.01/0.02 | Hexane | 125 | 4 | 81 | 40 | 51.1 | 4.4 |
| 18 | 0.11 | 0.11 | 0.0005 | $(WCl_6)$ 0.01 | $C_6H_5Cl$ | 70 | 4 | 108 | 70 | 33.6 | 5.8 |
| 19 | 0.42 | 0.42 | 0.002 | 0.02/0.04 | Hexane | 180 | 4.5 | 77 | 80 | 40.5 | 4.4 |
| 20 | 1.0 | 1.0 | 0.0025 | 0.05/0.1 | None | | 20 | 80 | — | 23.0 | 5.0 |

*$SnCl_4/GeCl_4$ the metal halide employed (compare Runs 7 and 20), (5) solvent employed (compare Runs 16 and 22, 20 and 21); (6) the amount of solvent employed (compare Runs 21, and 29); (7) reaction pressure (compare Runs 26 and 27).

EXAMPLE II

Synthesis of 5-Decene

An oven-dried 2-L, 3-neck round bottom flask was equipped with a magnetic stirrer and a reflux condenser. The condenser outlet was connected to a mercury filled bubble tube capped with a $CaSO_4$ drying tube. The open necks of the reaction flask were capped with septa. The reagents were charged via syringe through the septum, then the vessel was heated to 80° C. for 24 hours.

In an exemplary reaction, 672 g (8 mol) of hexene were reacted in the presence of 0.0045 mol (methoxyphenyl)pentacarbonyltungsten(O), 0.10 mol $SnCl_4$ and 0.15 mol $SiCl_4$ with about 100 mL chlorobenzene as solvent. After 24 hours, reaction mixture was treated with aqueous ammonium hydroxide, extracted, and distilled. An isolated yield of 46% was obtained. The 5-decene had a trans to cis ratio of about 4:1.

EXAMPLE III

9-Tetradecenyl Acetate from 5-Decene and 9-Decenyl Acetate

A series of runs were carried out for the preparation of 9-tetradecenyl acetate from 5-decene having a trans/cis ratio of about 4:1 and 9-decenyl acetate. The carbene employed was (methoxyphenylcarbene)pentacarbonyltungsten(O), and the metal halide catalyst component, The results in Table II demonstrate the higher trans/cis ratios obtained as a result of substituting the internal olefin, 5-decene, for the alpha-olefin 1-hexene of Example I. A typical trans/cis ratio of 5:1 or greater is obtained upon reaction of 5-decene with 9-decenyl acetate.

EXAMPLE IV

Preparation of 1,18-Diacetoxy-9-Octadecene

The 300 mL autoclave was charged with 9-decenyl acetate (0.22 mol), (phenylmethoxycarbene)pentacarbonyltungsten(O) (0.001 mol), $SnCl_4$ (0.01 mol), $SiCl_4$ (0.02 mol) and 20 mL chlorobenzene. The autoclave was heated to 86° for 4 hours with continuous venting above 5 psig.

The reaction product, following removal of catalyst components, was vacuum distilled at 35 mm Hg. Material boiling between 205°-230° C. was collected and found to be pure 1,18-diacetoxy-9-octadecene. The trans/cis ratio of distilled product was 1.7.

The crude reaction product was purified by standard crystallization techniques from ethanol solvent. The crystals so obtained were collected by filtration, analyzed, and found to be essentially pure trans-1,18-diacetoxy-9-octadecene.

EXAMPLE V

9-Tetradecenyl Acetate from 1-Hexene and trans-1,18-Diacetoxy-9-Octadecene

A series of runs were carried out for the preparation of 9-tetradecenyl acetate from 1-hexene and the trans-1,18-diacetoxy-9-octadecene prepared as set forth in the preceding example. The carbene employed for the disproportionation of the acetate was (methoxyphenylcarbene)pentacarbonyltungsten(O), and the metal halide catalyst component consisted of a mixture of $SnCl_4$ and $SiCl_4$. The acetate product obtained was essentially all trans.

EXAMPLE VI

9-Tetradecenyl Acetate from 5-Decene and trans-1,18-Diacetoxy-9-Octadecene

A series of runs were carried out for the preparation of 9-tetradecenyl acetate from 5-decene having a trans/cis ratio of about 4:1 and trans-1,18-diacetoxy-9-octadecene. Unless otherwise noted, the carbene employed was (methoxyphenylcarbene)pentacarbonyltungsten(O), and the metal halide catalyst component consisted of a mixture of $SnCl_4$ and $SiCl_4$. As in Example V, essentially all trans product was obtained.

EXAMPLE VII

9-Tetradecenyl Acetate from Mixed Cis/Trans-1,18-Diacetoxy-9-Octadecene

9-Tetradecenyl Acetate from Mixed Cis/Trans 1,18-Diacetoxy-9-Octadecene

A series of runs were carried out for the preparation of 9-tetradecenyl acetate from 1-hexene or a trans/cis mixture of 5-decene and 1.7/1 trans/cis mixture of 1,18-diacetoxy-9-octadecene. The carbene employed was (methoxyphenylcarbene)pentacarbonyltungsten(O), and the metal halide component consisted of a mixture of $SnCl_4$ and $SiCl_4$. Reagent quantities reacted, reaction conditions and reaction results are presented in Table III.

TABLE III

| Run # | Alkene, Mol | Acetate, Mol | Catalyst, Mol Carbene | $SnCl_4/SiCl_4$ | Diluent, ml | Time Hrs. | Temp. °C. | Press., psig | Yield | Trans/Cis |
|---|---|---|---|---|---|---|---|---|---|---|
| 1 | 1-Hexene, 0.44 | 0.22 | 0.001 | 0.011/0.022 | $C_6H_5Cl$ 120 | 4 | 92 | 30 | 16.3 | 4.4 |
| 2 | 5-Decene, 0.44 | 0.22 | 0.001 | 0.011/0.022 | $C_6H_5Cl$ 120 | 4 | 96 | 15 | 3.1 | 5.5 |
| 3 | 5-Decene, 0.44 | 0.19 | 0.001 | 0.011/0.022 | $C_6H_5Cl$ 120 | 4 | 91 | 15 | 10.9 | 5.8 |

The results in Table III demonstrate when trans/cis mixture 1,18-diacetoxy-9-octadecene is employed, less trans isomer is obtained than when the octadecene reactant is substantially all trans. The trans level is slightly higher with the internal olefin reactant than the alpha-olefin reactant.

EXAMPLE VIII

9-Tetradecenyl Acetate from 1-Hexene and Oleyl Acetate

A series of runs were carried out for the preparation of 9-tetradecenyl acetate from 1-hexene and oleyl acetate. The carbene employed was (methoxyphenylcarbene)pentacarbonyltungsten(O), and the metal halide catalyst component consisted of a mixture of $SnCl_4$ and $SiCl_4$. Reagent quantities reacted, reaction conditions and reaction results are presented in Table IV.

TABLE IV

| Run # | 1-Hexene, Mol | Acetate, Mol | Catalyst, Mol Carbene | $SnCl_4/SiCl_4$ | Diluent, ml | Time Hrs. | Temp., °C. | Press., psig | Yield | Trans/Cis |
|---|---|---|---|---|---|---|---|---|---|---|
| 1 | 0.44 | 0.11 | 0.0005 | 0.011/0.022 | $C_6H_5Cl$ 60 | 4 | 109 | 40 | 7.1 | 6.5 |
| 2 | 0.44 | 0.11 | 0.0005 | 0.011/0.022 | $C_6H_5Cl$ 60 | 4 | 108 | 40 | 8.1 | 2.1 |
| 3 | 0.44 | 0.11 | 0.0005 | 0.011/0.022 | $C_6H_5Cl$ 60 | 2 | 107 | 200 | 7.8 | 1.6 |
| 4 | 0.44 | 0.22 | 0.0005 | 0.011/0.022 | $C_6H_5Cl$ 30 | 2.25 | 105 | 185 | 3.8 | 1.5 |

On the average, a low trans/cis ratio product was obtained.

EXAMPLE IX

9-Tetradecenyl Acetate from 5-Decene and Oleyl Acetate

A series of runs were carried out for the preparation of 9-tetradecenyl acetate from a trans/cis mixture of 5-decene and oleyl acetate. The carbene employed was (methoxyphenylcarbene)pentacarbonyltungsten(O), and the metal halide catalyst component consisted of a mixture of $SnCl_4$ and $SiCl_4$. Reagent quantities reacted, reaction conditions and reaction results are presented in Table V.

TABLE V

| Run # | 5-Decene, Mol | Acetate, Mol | Catalyst, Mol Carbene | $SnCl_4/SiCl_4$ | Diluent, ml | Time Hrs. | Temp., °C. | Press., psig | Yield | Trans/Cis |
|---|---|---|---|---|---|---|---|---|---|---|
| 1 | 0.4 | 0.11 | 0.0005 | 0.011/0.022 | $C_6H_5Cl$ 60 | 4.5 | 105 | 10 | 6.3 | 2.1 |
| 2 | 0.4 | 0.11 | 0.0005 | 0.011/0.022 | $C_6H_5Cl$ 60 | 4.5 | 92 | 100 | 9.8 | 12.3 |

The results in Table V demonstrate if 5-decene is employed it is possible to obtain a higher trans/cis ratio than when oleyl acetate was reacted with 1-hexene.

EXAMPLE X

9-Dodecenyl Acetate from 1-Butene and 9-Decenyl Acetate

A series of runs were carried out for the preparation of 9-dodecenyl acetate from 1-butene and 9-decenyl acetate. The carbene employed was (methoxyphenylcarbene)pentacarbonyltungsten(O). Runs were made using each of the metal halide catalyst components, i.e., $WCl_6$, or a mixture of $SnCl_4$ and $SiCl_4$, or a mixture of $SnCl_4$ and $GeCl_4$. Trans/cis ratios of 1.2–5.0 were obtained with a 1.7 average.

EXAMPLE XI

9-Dodecenyl Acetate from 1-Butene and Oleyl Acetate

A series of runs were carried out wherein 9-dodecenyl acetate was prepared from 1-butene and oleyl acetate. The carbene employed was (methoxyphenylcarbene)pentacarbonyltungsten(O), and the metal halide was $WCl_6$ or a mixture of $SnCl_4$ and $SiCl_4$. The trans/cis ratios were in the range of 1.1 to 1.2/1. For the best results in terms of yield excess 1-butene was needed.

EXAMPLE XII

9-Dodecenyl Acetate from 3-Hexene and 9-Decenyl Acetate

Several runs were carried out for the preparation of 9-dodecenyl acetate from 3-hexene and 9-decenyl acetate. The carbene employed was (methoxyphenylcarbene)pentacarbonyltungsten(O), and the metal halide catalyst component consisted of a mixture of $SnCl_4$ and $SiCl_4$. Reagent quantities employed, reaction conditions and reaction results are presented in Table VI.

the metal halide catalyst component consisted of a mixture of $SnCl_4$ and $SiCl_4$. Reagent quantities employed, reaction conditions and reaction results are presented in Table VII.

TABLE VII

| Run # | Alkene, Mol | Formate, Mol | Catalyst, Mol Carbene | Catalyst, Mol $SnCl_4/SiCl_4$ | Diluent, ml | | Time Hrs. | Temp., °C. | Press., psig | Yield | Trans/Cis |
|---|---|---|---|---|---|---|---|---|---|---|---|
| 1 | 1-Hexene, 0.22 | 0.11 | 0.002 | 0.02/0.04 | Hexane | 100 | 5 | 103 | 80 | 7.4 | 1.8 |
| 2 | 1-Hexene, 0.89 | 0.44 | 0.002 | 0.02/0.04 | $C_6H_5Cl$ | 200 | 4.5 | 78 | 5 | trace | — |
| 3 | 5-Decene, 0.26 | 0.11 | 0.001 | 0.01/0.02 | Hexane | 80 | 4 | 107 | 55 | 3.0 | ~20.0 |
| 4 | 5-Decene, 0.22 | 0.11 | 0.001 | 0.01/0.02 | $C_6H_5Cl$ | 125 | 5 | 102 | 50 | 28.1 | — |
| 5 | 5-Decene, 0.11 | 0.22 | 0.001 | 0.01/0.02 | Hexane | 150 | 4 | 101 | 45 | trace | — |

The results in Table VII demonstrate that the ratio of olefin reactants to the carbene catalyst can effect the yield. In the reactions in which the yield was significant, the alpha-olefin (1-hexene) gave 9-tetradecenyl formate with a trans/cis ratio of about 2/1 while the internal olefin (5-decene) gave 9-tetradecenyl formate with a trans/cis ratio of about 20/1.

EXAMPLE XV

9-Tetradecenyl Propionate from 9-Decenyl Propionate

Two cross-disproportionation reactions of 9-decenyl propionate were carried out employing 1-hexene and 5-decene. The carbene catalyst employed was (methoxyphenylcarbene)pentacarbonyltungsten(O), and the metal halide catalyst component consisted of a mixture of $SnCl_4$ and $SiCl_4$. The molar ratio of the 9-decenyl propionate to the carbene was 220/1. The molar ratio of

TABLE VI

| Run # | 3-Hexene, Mol | Acetate, Mol | Catalyst, Mol Carbene | Catalyst, Mol $SnCl_4/SiCl_4$ | Diluent, ml | | Time Hrs. | Temp., °C. | Press., psig | Yield | Trans/Cis |
|---|---|---|---|---|---|---|---|---|---|---|---|
| 1 | 0.5 | 0.25 | 0.0005 | 0.005/0.01 | $C_6H_5Cl$ | 60 | 4 | 105 | 50 | 7.8 | 5.2 |
| 2 | 1.61 | 0.25 | 0.002 | 0.01/0.02 | $C_6H_5Cl$ | 120 | 6 | 90 | 40 | 69.1 | 5.4 |
| 3 | 1.61 | 0.25 | 0.002 | 0.01/0.02 | $C_6H_5Cl$ | 20 | 6 | 87 | 40 | ~70.0 | 5.3 |
| 4 | 3.22 | 0.50 | 0.002 | 0.02/0.04 | $C_6H_5Cl$ | 220 | 5 | 92 | 40 | — | 5.4 |
| 5 | 3.22 | 0.50 | 0.002 | 0.02/0.04 | $C_6H_5Cl$ | 220 | 6 | 84 | 35 | 44.4 | 5.4 |

The results in Table VI demonstrate that the trans/cis ratio of 9-dodecenyl acetate typically obtained with the internal olefin, 3-hexene is significantly higher than that normally obtained with the terminal olefin, 1-butene.

EXAMPLE XIII

9-Tetradecenyl Acetate and 9-Undecenyl Acetate from 9-Decenyl Acetate and 2-Heptene Several runs were carried out employing cis- or trans-2-heptene with 9-decenyl acetate or 1,18-diacetoxy-9-octadecene having a trans to cis ratio of 1.7:1 in the presence of (methoxyphenylcarbene)pentacarbonyltungsten(O) and $SnCl_4$ plus $SiCl_4$ as the metal halide catalyst component.

The trans/cis ratio of the 9-tetradecenyl acetate was in the range of 2.6–3.4, for the 9-undecenyl acetate it was in the range of 1.6 to 4.9. The 2-heptene produced slightly less trans isomer than an internal symmetrical olefin. The cis isomer of 2-heptene produced even less trans product than the trans isomer of 2-heptene.

EXAMPLE XIV

9-Tetradecenyl Formate from 9-Decenyl Formate

Several runs were carried out for the preparation of 9-tetradecenyl formate from 9-decenyl formate and 1-hexene or 5-decene. The carbene employed was (methoxyphenylcarbene)pentacarbonyltungsten(O), and carbene to $SnCl_4$ was 10/1 and the molar ratio of $SiCl_4$ to $SnCl_4$ was 2/1. The 5-decene was employed in a 1/1 molar ratio with the propionate. The 1-hexene was employed at a 2/1 ratio.

The trans/cis ratio obtained with the 1-hexene was 1.8/1. The trans/cis ratio obtained with the 5-decene was 4.4/1.

EXAMPLE XVI

9-Tridecenyl Acetate from 9-Decenyl Acetate

Two cross-disproportionation reactions of 9-decenyl acetate were carried out with 1-pentene or trans-4-octene. The carbene employed was (methoxyphenylcarbene)pentacarbonyltungsten(O), and the metal halide catalyst component consisted of a mixture of $SnCl_4$ and $SiCl_4$. The relative amounts of olefins, carbene, $SnCl_4$ and $SiCl_4$ were as in the preceding example.

Here again the alpha-olefin produced a lower trans level than the internal olefin, namely 1.7/1 as compared to 12/1.

EXAMPLE XVII

9-Hexadecenyl Acetate from 9-Decenyl Acetate

Several runs were carried out for the preparation of 9-hexadecenyl acetate from 9-tetradecenyl acetate and 1-octene or 7-tetradecene. The carbene employed was (methoxyphenylcarbene)pentacarbonyltungsten(O), and the metal halide component consisted of a mixture of $SnCl_4$ and $SiCl_4$.

The end product obtained with the terminal non-functional olefin was relatively low in trans content about 1.8 trans to cis. The trans content of the product obtained with the internal olefin was not determined.

EXAMPLE XVIII

4-Nonenyl Acetate from 5-Pentenyl Acetate and 1-Hexane or 5-Decene

Two cross-disproportionation reations of 5-pentenyl acetate were carried out with 1-hexene or 5-decene as the second reactant. The carbene employed was (methoxyphenylcarbene)pentacarbonyltungsten(O), and the metal halide catalyst component consisted of a mixture of $SnCl_4$ and $SiCl_4$.

Again, the internal olefin was found to give a much higher trans- content product than does the terminal olefin reactant, 2.1/1 vs. 6.5/1 for these two reactions.

EXAMPLE XIX

Methyl-10-Pentadecenoate from Methyl-10-Undecenoate

Two cross-disproportionation reactions of methyl-10-undecenoate were carried out with 1-hexene or 5-decene as the second reactant. The carbene employed was (methoxyphenylcarbene)pentacarbonyltungsten(O), and the metal halide catalyst component consisted of a mixture of $SnCl_4$ and $SiCl_4$. Reagent quantities employed, reaction conditions and reaction results are presented in Table VIII.

TABLE IX

| Total Trap Catches | Commercial (4/1) | Inventive (½) | Control |
| --- | --- | --- | --- |
| 4/3–4/27 | 0 | 4 | 45 |
| 4/27–4/30 | 0 | 1 | 39 |
| 4/30–6/2 | 0 | 3 | 65 |
| % Tree Damage | 21.5 | 24.0 | 39.8 |

The results presented in Table IX demonstrate the effectiveness of a ½ cis/trans ratio of 9-dodecenyl acetate for the disruption of mating of Western Pine Shoot Borer. In addition, the reduction of tree damage is comparable to the reduction obtained with the commercially available 4/1 cis/trans 9-dodecenyl acetate.

EXAMPLE XXI

Field Tests—Tetradecenyl Formate

Three fields of cotton in a late fruiting stage were used to evaluate the effectiveness of tetradecenyl formate in controlling Heliothis species. In this case, the 9-tetradecenyl formate was prepared from 9-tetradecenyl acetate rather than directly from 9-decenyl formate. In a typical process 21.1 g (0.08 mol) of tetradecenyl acetate, 22.2 g (0.16 mol) $K_2CO_3$, 200 mL methanol, and 2 mL water were added to a 500 mL one neck round bottom flask. The mixture was stirred for two hours at room temperature. Then 200 mL of diethyl ether was added, and the mixture was filtered. The ether layer was washed with water, then saturated NaCl solution, then dried over $MgSO_4$. The dried solution was filtered and concentrated on a rotary evaporator. The product consisting of 9-tetradecenyl alcohol was then reacted with formic acid in benzene at gentle reflux (~80° C.)

TABLE VIII

| Run # | Alkene, Mol | Undecenoate, Mol | Catalyst, Mol Carbene | Catalyst, Mol $SnCl_4/SiCl_4$ | Diluent, ml | Time Hrs. | Temp., °C. | Press., psig | Yield | Trans/Cis |
| --- | --- | --- | --- | --- | --- | --- | --- | --- | --- | --- |
| 1 | 1-Hexene, 0.44 | 0.26 | 0.002 | 0.02/0.04 | $C_6H_5Cl$ 100 | 4.5 | 83 | 5 | 42.7 | 2.9 |
| 2 | 5-Decene, 0.26 | 0.26 | 0.002 | 0.02/0.04 | $C_6H_5Cl$ 100 | 5 | 82 | 60 | 66.9 | 4.0 |

The results again demonstrate that the internal olefin gives a product having a higher trans content than the alpha-olefin.

EXAMPLE XX

Field Tests 9-Dodecenyl Acetate

Three adjacent test plots 2000 ft wide and 4000 ft long in a ponderosa pine plantation in Oregon were used to evaluate a high trans-9-dodecenyl acetate product for its utility in controlling the Western Pine Shoot Borer, viz. Eucosoma sonomana. The first plot was treated with commercially available pheromone for the Western Pine Shoot Borer, i.e., a 4/1 cis/trans 9-dodecenyl acetate at a rate of 4 grams/acre using commercially available dispensing means such as those disclosed in U.S. Pat. No. 4,160,335 and U.S. Pat. No. 4,198,782. The middle plot was treated in the same manner and at the same rate with 9-dodecenyl acetate prepared according to the present invention. The 9-dodecenyl acetate had a cis/trans ratio of 1/2. The third plot was not treated with any 9-dodecenyl acetate in order to serve as a control. The applications were carried out during the week of 3/30/81 and trap catches 4/27–4/30 and 4/30–6/2/81. Tree damage was observed at the end of the growing season in the fall of 1981. Trap catch data and tree damage results are presented in Table IX.

for 24 hours. Then additional formic acid was added and the gentle reflux continued for another 24 hours. The 9-tetradecenyl formate was recovered by extraction.

Test plots measured 200 ft long and 100 ft wide and contained 60 rows. Plots were separated from each other by at least 200 ft down row and by 100 ft across rows. The test compound was laminated between ¼"×¼" plastic flakes. Plots were treated with formate at the rate of 10 grams/acre. The chemical was applied on 8/12/81 and 9/1/81 and insects were monitored on the nights of 8/12–14 and 9/1–9, respectively. Separate traps were put out for Heliothis zea and Heliothis virescens. Trap catch data are presented in Table X.

TABLE X

| Total Trap Catches | 5/1 | 2/1 | Control |
| --- | --- | --- | --- |
| 8/12–14 | | | |
| H. zea | 5 | 2 | 87 |
| H. virescens | 30 | 34 | 213 |
| 9/1–9 | | | |
| H. zea | 18 | 1 | 20 |
| H. virescens | 18 | 6 | 21 |

The results presented in Table X demonstrate the effectiveness, a 2/1 trans/cis ratio of 9-tetradecenyl formate for the disruption of mating of both Heliothis species. The 5/1 trans/cis ratio 9-tetradecenyl formate was also effective for disruption of mating Heliothis species.

EXAMPLE XXII

Field Tests—9-Tetradecenal

A 2/1 trans to cis ratio of 9-tetradecenal was evaluated in the same manner as was used in the preceding example. The 9-tetradecenal was prepared from 9-tetradecenyl alcohol prepared in the same manner as described in the preceding example. About 21 grams of the alcohol in a 50/50 weight ratio selection of dichloromethane was added dropwise to a flask charged with 43 g (0.2 mol) pyridinium chlorochromate, 20 g celite and 200 mL dichloromethane. The mixture was stirred at room temperature for about 2 hours after addition of the alcohol solution was complete. Then 200 mL of hexane was added and the mixture was filtered. The solvent was evaporated and the product vacuum distilled through a 2 ft. × $\frac{3}{4}$ in. packed column (Penn State stainless steel packing). A 36% yield of pure 9-tetradecenyl acetate was obtained.

The trap catch results are set forth in Table XI.

TABLE XI

| Total Trap Catches | Test Plot | Control Plot |
|---|---|---|
| 8/12–14 | | |
| H. zea | 1 | 87 |
| H. virescens | 44 | 213 |
| 9/1–9 | | |
| H. zea | 13 | 20 |
| H. virescens | 2 | 21 |

The results presented in Table XI demonstrate the effectiveness of a 2/1 trans/cis ratio of 9-tetradecenal for the disruption of mating of the Heliothis species.

EXAMPLE XXIII

Field Test—9-Hexadecenyl Alcohol

The effect of a 2/1 trans/cis mixture of 9-hexadecenyl alcohol on Heliothis species was tested in the same manner as described in Example XXI. The alcohol was prepared by the hydrolysis of 9-hexadecenyl acetate. The results are shown in Table XII.

TABLE XII

| Total Trap Catches | Test Plot | Control Plot |
|---|---|---|
| 8/12–14 | | |
| H. zea | 30 | 87 |
| H. virescens | 58 | 213 |
| 9/1–9 | | |
| H. zea | 10 | 20 |
| H. virescens | 56 | 21 |

The results presented in Table XII demonstrate the effectiveness of a 2/1 trans/cis ratio of 9-hexadecenyl alcohol for the description of mating of Heliothis zea. Results for the description of Heliothis virescens are mixed, the 9-hexadecenyl alcohol showing description activity is one test, but not in the other.

As will be evident to those skilled in the art, many variations and modifications of the present invention can be practiced in view of the foregoing disclosure without departing from the spirit and scope thereof.

What is claimed is:

1. A method for preparing a trans-rich internally unsaturated olefin having an oxygen-containing functional group comprising reacting (1) a symmetrical difunctional monoolefin in which the functional groups are terminal functional groups selected from the groups having the formulas

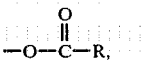

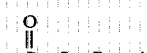

wherein R is a hydrocarbyl group having 1 to 20 carbon atoms or in the case of the first formula hydrogen with (2) a hydrocarbyl monoolefin consisting essentially of either an internal olefin or an alpha-olefin having at least three carbon atoms per molecule under suitable reaction conditions in the presence of a catalytic amount of a catalyst composition comprising effective amounts of (1) at least one neutral carbene complex having the formula

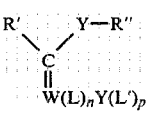

wherein R' is selected from the group consisting of alkyl or cycloalkyl radicals containing 1 to 10 carbons per radical and aryl or substituted aryl radicals containing 6 to 30 carbon atoms per radical wherein the substituted radicals can have one or more substituents, each of which can be the same or different and selected from the group consisting of halides, alkoxides, and alkyl radicals containing 1 to 20 carbon atoms per radical; wherein Y is S or O; R" is selected from the group consisting of alkyl, cycloalkyl, aryl, and substituted aryl radicals containing 1 to 30 carbon atoms per molecule and wherein the aryl substituents are as described for R' and wherein if Y is S only one of R' and R" can be aryl or substituted aryl; each L is a neutral ligand individually selected from CO, NO, PR'$_3$, PCl$_3$, PF$_3$, and pyridine, where R' is as defined above, and L' is cyclopentadienyl; p is 0 or 1; and n is 5 when p is 0 or 2 when p is 1; and (2) a metal component selected from the group consisting of the chlorides and bromides of the metals of Groups IVa, IVb, Vb, VIb, VIIb, VIII, and Ib and the oxychlorides and oxybromides of molybdenum, tungsten, vanadium, and chromium, wherein if the metal is vanadium it is in an oxidation state of either 4 or its highest, stable, common, ionic oxidation state; if the metal is molybdenum, tungsten, or rhenium it is in an oxidation state of either 5 or its highest, stable, common, ionic oxidation state; and if the metal is not vanadium, molybdenum, tungsten or rhenium the metal is in its highest, stable, common, ionic, oxidation state, characterized by the fact that the symmetrical difunctional olefin is substantially all in the trans form.

2. A process according to claim 1 wherein the functional monoolefin contains no more than 30 carbon atoms per molecule.

3. A process according to claim 2 wherein said functional monoolefin contains terminal groups of the formula $$\begin{array}{c} O \\ \parallel \\ -C-O-R. \end{array}$$

4. A process according to claim 1 wherein 9-tetradecenyl acetate is produced by reacting a functional olefin consisting essentially of trans-1,18-diacetoxy-9-octadecene with 1-hexene.

5. A process according to claim 1 wherein said functional olefin reactant consists essentially of the trans isomer of 1,18-diacetoxy-9-octadecene.

6. A process according to claim 5 wherein said hydrocarbyl monoolefin is selected from 1-hexene and 5-decene.

7. A method for producing an internally unsaturated functional olefin high in trans isomer comprising reacting (1) a functional monoolefin having at least one terminal functional group selected from groups having the formulas $$\begin{array}{c} O \\ \parallel \\ -O-C-R, \end{array}$$

$$\begin{array}{c} O \\ \parallel \\ -C-O-R, \text{ and} \end{array}$$

—OR wherein R is a hydrocarbyl group having 1 to 20 carbon atoms or in the case of the first formula hydrogen with (2) a hydrocarbyl monoolefin consisting of an acyclic internal olefin under suitable reaction conditions in the presence of a catalytic amount of a catalyst composition comprising effective amounts of (1) at least one neutral carbene complex having the formula $$\begin{array}{c} R' \diagdown \diagup Y-R'' \\ C \\ \parallel \\ W(L)_n Y(L')_p \end{array}$$

wherein R' is selected from the group consisting of alkyl or cycloalkyl radicals containing 1 to 10 carbons per radical and aryl or substituted aryl radicals containing 6 to 30 carbon atoms per radical wherein the substituted radicals can have one or more substituents, each of which can be the same or different and selected from the group consisting of halides, alkoxides, and alkyl radicals containing 1 to 20 carbon atoms per radical; wherein Y is S or O; R" is selected from the group consisting of alkyl, cycloalkyl, aryl, and substituted aryl radicals containing 1 to 30 carbon atoms per molecule and wherein the aryl substituents are as described for R' and wherein if Y is S only one of R' and R" can be aryl or substituted aryl; each L is a neutral ligand individually selected from CO, NO, PR'$_3$, PCl$_3$, PF$_3$, and pyridine, where R' is as defined above, and L' is cyclopentadienyl; p is 0 or 1; and n is 5 when p is 0 or 2 when p is 1; and (2) a metal component selected from the group consisting of the chlorides and bromides of the metals of Groups IVa, IVb, Vb, VIb, VIIb, VIII, and Ib and the oxychorides and oxybromides of molybdenum, tungsten, vanadium, and chromium, wherein if the metal is vanadium it is in an oxidation state of either 4 or its highest, stable, common, ionic oxidation state; if the metal is molybdenum, tungsten, or rhenium it is in an oxidation state of either 5 or its highest, stable, common, ionic oxidation state; and if the metal is not vanadium, molybdenum, tungsten or rhenium the metal is in its highest, stable, common, ionic, oxidation state.

8. A process according to claim 7 wherein said neutral carbene complex is selected from those wherein R' is selected from phenyl or an alkyl group having 1 to 10 carbon atoms; R" is an alkyl radical having 1 to 10 carbon atoms; Y is O, L is CO, n is 5, and p is 0.

9. A process according to claim 8 wherein said metal component of said catalyst comprises a mixture of SnCl$_4$ and either SiCl$_4$ or GeCl$_4$.

10. A process according to claim 9 wherein the olefinic hydrocarbyl portion of said functional monoolefin has the formula $$R'''-CH=CH(CH_2)_n-$$

wherein n is in the range of 2 to 10, R''' is hydrogen or an alkyl radical having 1 to 20 carbon atoms.

11. A process according to claim 9 wherein said functional monoolefin is selected from the group consisting of 9-decenyl acetate, oleyl acetate, 1,18-diacetoxy-9-octadecene, 9-decenyl formate, 9-decenyl propionate, 5-pentenyl acetate, and methyl-10-undecenoate.

12. A process according to claim 11 wherein said internal olefin is selected from the group consisting of 5-decene, 2-butene, 3-hexene, 4-octene, and 7-tetradecene.

13. A process according to claim 10 wherein 9-dodecenyl acetate is produced by reacting 9-decenyl acetate and 3-hexene.

14. A process according to claim 10 wherein 9-tridecenyl acetate is produced by reacting 9-decenylacetate and trans-4-octene.

15. A process according to claim 11 wherein said internal olefin is 5-decene produced by the self-disproportionation of 1-hexene in the presence of the same catalyst specified for the reaction of the functional olefin.

16. A process for preparing 9-tetradecenyl formate by reacting 1-hexene or 5-decene with 9-decenyl acetate in accordance with the method of claim 7 to obtain 9-tetradecenyl acetate, then reacting the acetate with water to obtain the corresponding alcohol and then reacting the alcohol with formic acid to obtain the formate.

17. A process for preparing 9-hexadecenyl alcohol by reacting 1-octene or 7-tetradecene with 9-decenyl acetate in accordance with the method of claim 7 to obtain 9-hexadecenyl acetate and then reacting the acetate with water to obtain the corresponding alcohol.

18. A process for preparing 9-tetradecenyl alcohol by reacting 1-hexene or 5-decene with 9-decenyl acetate in accordance with the method of claim 7 to obtain tetradecenyl acetate and then reacting the acetate with water to obtain said alcohol.

19. A process for preparing 9-tetradecenal comprising preparing 9-tetradecenyl alcohol in accordance with claim 18 and oxidizing the alcohol to the aldehyde.

* * * * *